(12) United States Patent
Sato et al.

(10) Patent No.: US 7,545,279 B2
(45) Date of Patent: Jun. 9, 2009

(54) CONDITION-ANALYZING DEVICE

(75) Inventors: Isao Sato, Yokohama (JP); Tomofumi Nishiura, Yokohama (JP); Masato Nakajima, Yokohama (JP); Kazuhiro Mimura, Tokyo (JP); Yasuhiro Takemura, Tokyo (JP); Kei Katou, Tokyo (JP); Toshiharu Takesue, Tokyo (JP)

(73) Assignees: Sumitomo Osaka Cement Co., Ltd., Tokyo (JP); Keio University, Tokyo (JP)

( * ) Notice: Subject to any disclaimer, the term of this patent is extended or adjusted under 35 U.S.C. 154(b) by 213 days.

(21) Appl. No.: 10/560,027

(22) PCT Filed: Jun. 3, 2004

(86) PCT No.: PCT/JP2004/007716

§ 371 (c)(1),
(2), (4) Date: May 24, 2006

(87) PCT Pub. No.: WO2004/009227

PCT Pub. Date: Dec. 16, 2004

(65) Prior Publication Data

US 2006/0279428 A1    Dec. 14, 2006

(30) Foreign Application Priority Data

Jun. 9, 2003    (JP)    ............................. 2003-163502

(51) Int. Cl.
*G03H 1/02*    (2006.01)
*G08B 23/00*    (2006.01)

(52) U.S. Cl. .................. 340/573.1; 340/575; 359/28

(58) Field of Classification Search ............ 340/575, 340/573.1, 539.12–539.15, 573; 359/3, 28, 359/33; 348/143–161; 382/103
See application file for complete search history.

(56) References Cited

U.S. PATENT DOCUMENTS 4,882,566 A * 11/1989 Koerber et al. ......... 340/825.69

(Continued)

FOREIGN PATENT DOCUMENTS

EP    0 919 184 A1    6/1999

(Continued)

*Primary Examiner*—Toan N Pham
*Assistant Examiner*—Jennifer Mehmood
(74) *Attorney, Agent, or Firm*—Foley & Lardner LLP

(57) ABSTRACT

A condition analysis apparatus capable of grasping the condition of an object easily and accurately is provided. The condition analysis apparatus 1 includes a three-dimensional sensor 10 for measuring sampling-point-moves in the height direction of an object 2 existing in a target area at a plurality of sampling points, and area definition means 22 for defining an area where a plurality of the sampling-point-moves are in the generally same phase. The thus constructed condition analysis apparatus 1 can grasp the condition of the object 2 easily and accurately. Preferably, the condition analysis apparatus 1 includes information output means 40 for outputting information of an area including the area defined by the area definition means 22.

8 Claims, 14 Drawing Sheets

U.S. PATENT DOCUMENTS

| | | | | |
|---|---|---|---|---|
| 4,947,152 A | * | 8/1990 | Hodges | 340/573.4 |
| 5,471,198 A | * | 11/1995 | Newham | 340/573.4 |
| 5,479,939 A | * | 1/1996 | Ogino | 600/595 |
| 5,914,660 A | * | 6/1999 | Mesibov et al. | 340/573.7 |
| 6,011,477 A | * | 1/2000 | Teodorescu et al. | 340/573.1 |
| 6,049,281 A | * | 4/2000 | Osterweil | 340/573.4 |
| 7,106,885 B2 | * | 9/2006 | Osterweil et al. | 382/103 |
| 7,110,569 B2 | * | 9/2006 | Brodsky et al. | 382/103 |
| 7,167,575 B1 | * | 1/2007 | Nichani et al. | 382/103 |

FOREIGN PATENT DOCUMENTS

| | | |
|---|---|---|
| JP | 2002-175582 A | 6/2002 |
| JP | 2003-32672 A | 1/2003 |

* cited by examiner

IMAGE OF BRIGHT SPOT

FIG. 12

| CHEYNE-STOKES BREATHING | DISORDERS IN THE BOTH SIDES OF CEREBRAL SUBCORTICES AND IN DIENCEPHALON |
|---|---|
| CENTRAL HYPERVENTILATION | DISORDERS FROM LOWER MESENCEPHALON TO UPPER PONS |
| ATAXIC BREATHING | DISORDERS FROM LOWER PONS TO UPPER MEDULLA OBLONGATA |
| KUSSMAUL BREATHING | DIABETIC COMA OR UREMIA |

IMAGE OF BRIGHT LINE

CONDITION-ANALYZING DEVICE

BACKGROUND OF THE INVENTION

1. Field of the Invention

The present invention relates to a condition analysis apparatus, and in particular to a condition analysis apparatus capable of easily and accurately grasping the condition of an object.

2. Description of Related Art

Movement detection sensors have so far been proposed as movement detection devices for detecting the movement of an object such as a person, in a space such as a bathroom. As a typical example, there has been a monitoring apparatus for monitoring the breath of a sleeping person on a bed by projecting a pattern onto the sleeping person on the bed, continuously taking an image of the projected pattern, and calculating the shift amount of the pattern from the image taken continuously (see Patent Document 1, for example).

Patent Document 1: JP-A-2002-175582 (pp 5-9 and FIGs. 1-13)

With the conventional apparatus as described above, however, the condition of each part of the object, such as a moving direction, is difficult to accurately grasp.

SUMMARY OF THE INVENTION

It is therefore an object of the present invention to provide a condition analysis apparatus capable of easily and accurately grasping the condition of an object.

Means for Solving the Problem

In order to achieve the foregoing object, a condition analysis apparatus according to one aspect of the present invention comprises, as shown for example in FIGS. 1 and 4, a three-dimensional sensor 10 for measuring, at a plurality of sampling points, sampling-point-moves in a height direction of an object existing in a target area; and area definition means 22 for defining an area where a plurality of the sampling-point-moves are in the generally same phase.

The thus constructed condition analysis apparatus includes the 3-D sensor 10 and the area definition means 22. Sampling-point-moves in the height direction of the object 2 existing in the target area are measured at a plurality of sampling points, and an area where a plurality of the sampling-point-moves measured are in the generally same phase is defined. Thus, the condition analysis apparatus can easily and accurately grasp the condition of the object.

According to another aspect of the present invention, the condition analysis apparatus 1 preferably comprises information output means 40 for outputting information of an area including the area defined by the area definition means 22.

According to still another aspect of the present invention, in the condition analysis apparatus 1, the three-dimensional sensor 10 has a projection device 11 for projecting a light pattern on the target area; a image capturing apparatus 12 for capturing an image of the target area while the light pattern is projected thereon; and measurement means 14 for measuring shifts of the pattern on the captured images, wherein sampling-point-moves in the height direction of the object 2 are measured at the plurality of sampling points based on the shifts of the pattern measured.

The thus constructed condition analysis apparatus includes the projection device 11, the image capturing apparatus 12, and the measurement means 14. The target area is image-captured while the light pattern is projected thereon, shifts of the pattern on the captured images are measured, and sampling-point-moves in the height direction of the object 2 are measured at the plurality of sampling points based on the shifts of the pattern measured. Thus, it is possible to accurately measure the sampling-point-moves in the height direction of the object 2 at the plurality of sampling points with a simple construction.

According to still another aspect of the present invention, in the condition analysis apparatus 1, if a specific number or more of the sampling points in a specific area represent sampling-point-moves in the same specific type of phase, the area definition means 22 preferably defines the specific area as an area where the sampling-point-moves in the specific type of phase are occurring.

With this construction, if a predetermined specific number or more of the sampling points in a specific area represent sampling-point-moves in the same, specific type of phase, the area definition means 22 defines the specific area as an area where the sampling-point-moves in the specific type of phase are occurring. Thus, the phases of sampling-point-moves in respective parts of the object 2 can be distinguished, for example.

According to still another aspect of the present invention, in the condition analysis apparatus 1, the area definition means 22 may search a specific area for sampling points representing sampling-point-moves in the same specific type of phase, form a group of sampling points representing the sampling-point-moves in the generally same phase based on the search results, and define the formed group of sampling points as an area where the sampling-point-moves in the generally same phase are occurring.

According to still another aspect of the present invention, the condition analysis apparatus 1 may comprise anomaly determination means 26 for determining an anomaly of the object 2 based on the area defined by the area definition means 22.

Effect of the Invention

As described above, the present invention comprises a three-dimensional sensor for measuring, at a plurality of sampling points, sampling-point-moves in a height direction of an object existing in a target area and area definition means for defining an area where a plurality of the sampling-point-moves are in the generally same phase, and there is provided the condition analysis apparatus which can easily and accurately grasp the condition of the object.

This application is based on the Patent Applications No. 2003-163502 filed on Jun. 9, 2003 in Japan, the contents of which are hereby incorporated in its entirety by reference into the present application, as part thereof.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

BRIEF DESCRIPTION OF THE DRAWINGS

FIG. 8(a) shows downward sampling-point-moves in the abdomen and FIG. 8(b) shows upward sampling-point-moves in the thorax.

FIG. 12 is a drawing showing a table of the names of diseases and the diseased locations corresponding to the waveform patterns representing the abnormal breaths of FIG. 11.

DESCRIPTION OF REFERENCE NUMERALS AND SYMBOLS

Figure 1:
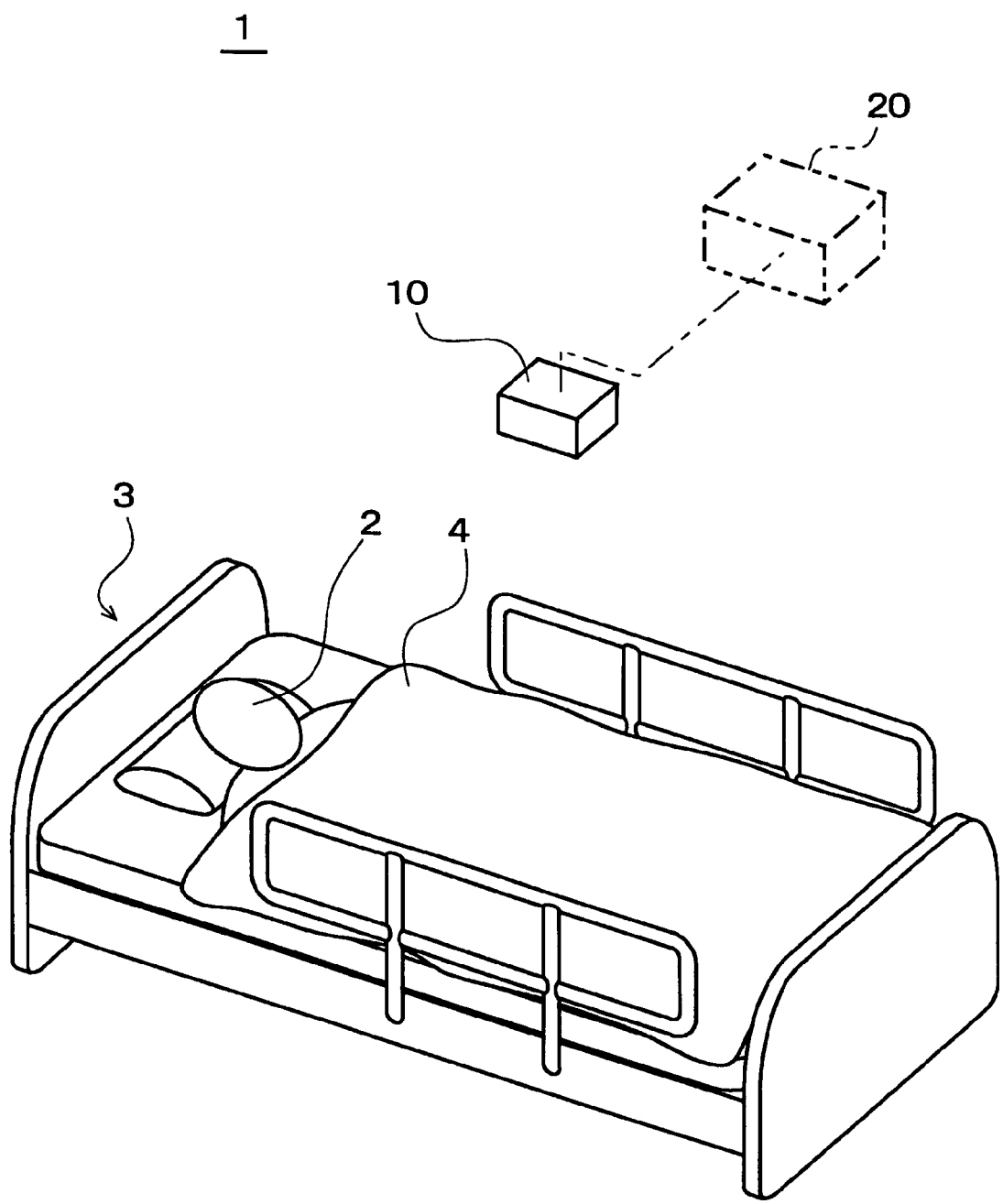
FIG. 1. is a schematic view of the external appearance of a monitoring apparatus according to an embodiment of the present invention.

1: monitoring apparatus
2: person
3: bed
4: blanket
10: FG sensor (3-D sensor)
11: projection device
11a: pattern
11b: bright spot
12: image capturing apparatus
14: measurement device
20: computing device
21: control section
22: area definition section
23: 3-D shape generation section
24: output information generation section
25: movement discrimination section
26: anomaly determination section
40: display
102: flat surface
103: solid
105: light beam generation section
120: grating
121: optical fiber
122: FG element

DETAILED DESCRIPTION OF PREFERRED EMBODIMENTS

FIG. 1 schematically shows the external appearance of a monitoring apparatus 1 as a condition analysis apparatus according to an embodiment of the present invention. The monitoring apparatus 1 includes a 3-D sensor 10 for measuring sampling-point-moves in the height direction of an object, existing in a target area, at a plurality of sampling points, and a computing device 20 for controlling the monitoring apparatus 1. The monitoring apparatus 1 also monitors the target area. In this embodiment, the object is one that breathes. That is, the object is a person or an animal, for example. In this embodiment, the object is to be a person 2. Also, in this embodiment, the target area is the top of a bed 3. The 3-D sensor 10 can also measure the height at the respective sampling points in the target area.

In the drawing, the person 2 lies on the bed 3. A blanket 4 is placed over the person 2, covering a part of the person 2 and a part of the bed 3. In this case, the 3-D sensor 10 measures sampling-point-moves in the height direction of the upper side of the blanket 4. In a case where the blanket 4 is not used, the 3-D sensor 10 measures sampling-point-moves in the height direction of the person 2 itself.

The 3-D sensor 10 is disposed over the bed 3. The 3-D sensor 10 will be described in detail later. In the drawing, the 3-D sensor 10 and the computing device 20 are separate components. However, they may be constructed integrally. This allows the monitoring apparatus 1 to be downsized. The computing device 20 is typically a computer such as a personal computer.

Figure 2:
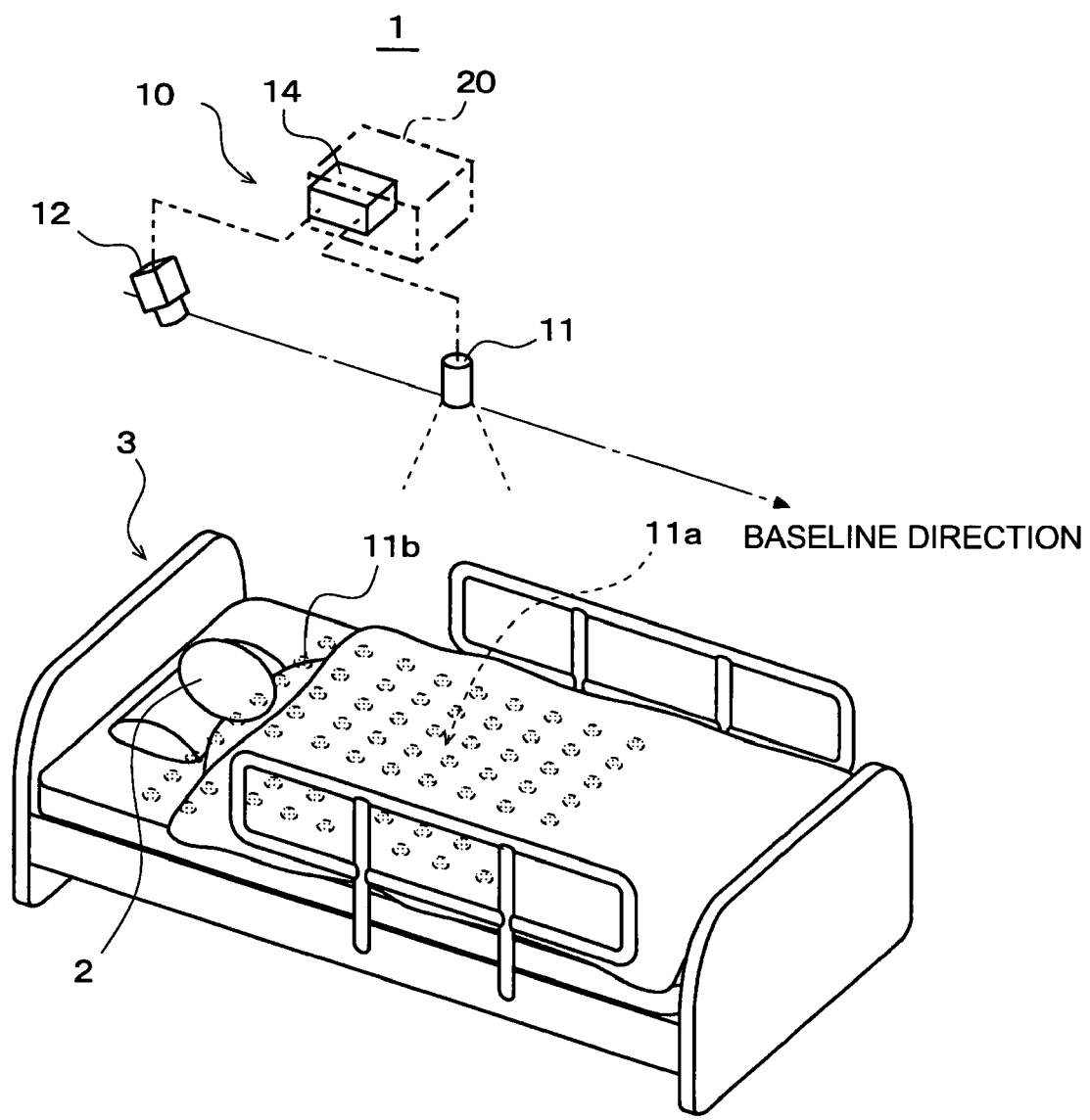
FIG. 2 is a schematic view of the external appearance of the monitoring apparatus, using an FG sensor as a 3-D sensor, according to the embodiment of the present invention.

With reference to the schematic external view of FIG. 2, the 3-D sensor 10 is described. In this embodiment, an FG sensor to be described later is used in the 3-D sensor 10. Hereinafter, the 3-D sensor 10 is described as an FG sensor 10. The FG sensor 10 includes a projection device 11 for projecting a light pattern on the target area, namely the bed 3, a image capturing apparatus 12 for capturing an image of the top of the bed 3 while the light pattern is projected thereon, and a measurement device 14 as measurement means for measuring shifts of the pattern on images captured by the image capturing apparatus 12. The measurement device 14 also measures sampling-point-moves in the height direction of the person 2 at the plurality of sampling points based on the shifts of the pattern measured. The projection device 11 and the image capturing apparatus 12 are electrically connected to and hence controlled by the measurement device 14. In this embodiment, the measurement device 14 is constructed integrally with the computing device 20. The light pattern to be projected includes a plurality of bright spots. The plurality of bright spots projected on the bed 3 respectively correspond to the plurality of sampling points on the bed 3. The image capturing apparatus 12 is typically a CCD camera. The respective components are described below.

Figure 3:
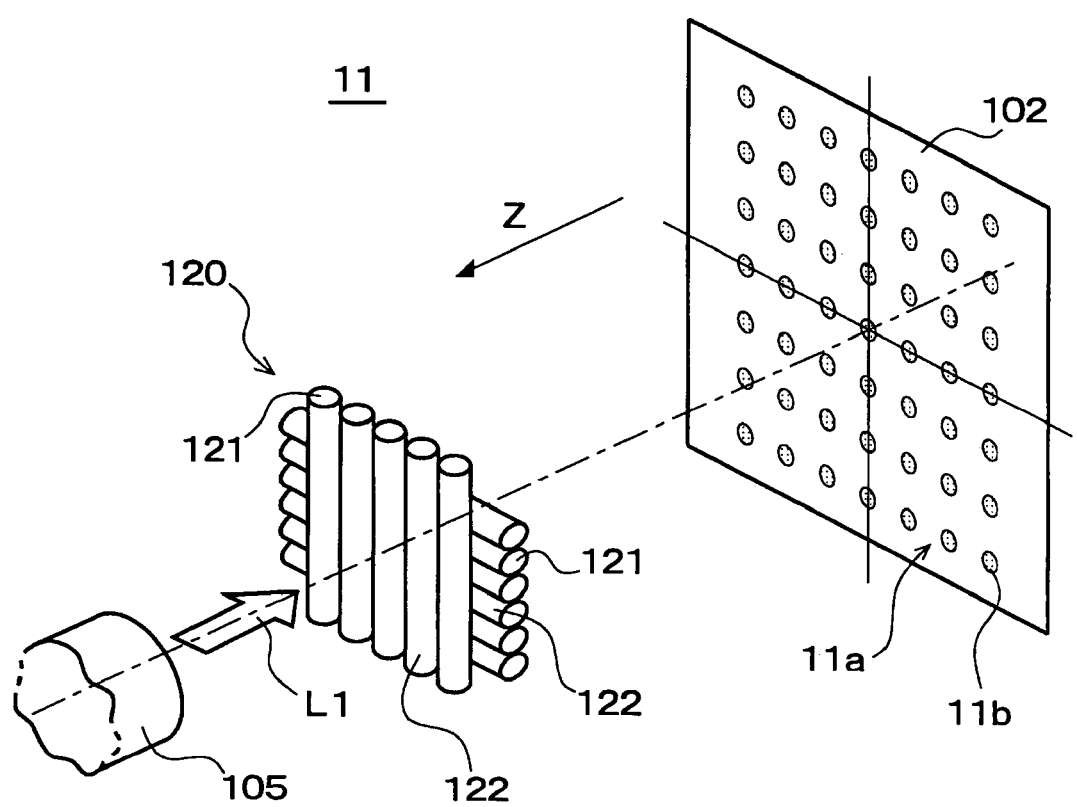
FIG. 3 is a schematic perspective view illustrating a projection device according to the embodiment of the present invention.

With reference to the schematic perspective view of FIG. 3, the projection device 11 suitable for the monitoring apparatus 1 is described. Here, a laser beam L1 to be described later is projected perpendicularly on a flat surface 102 as the target area, for illustration purposes. The projection device 11 includes a light beam generation section 105 as light beam generation means for generating a coherent light beam, and a fiber grating 120 (hereinafter simply referred to as grating 120). The coherent light beam projected by the light beam generation section 105 is typically an infrared laser. The light beam generation section 105 generates a parallel light beam. The light beam generation section 105 is typically a semiconductor laser device including a collimator lens (not shown in the drawing), which generates a parallel light beam, namely the laser beam L1. The laser beam L1 has a generally circular cross section. When referring to as a parallel light beam, it may be substantially parallel and includes approximately parallel light beams.

The grating 120 is disposed parallel to the flat surface 102 (perpendicular to the Z-axis). The laser beam L1 is incident on the grating 120 in the Z-axis direction. Then, the laser beam L1 is condensed within a plane of each of the individual optical fibers 121 having the lens effect, and spread as divergent waves to cause interference, resulting in a pattern 11a, or an array of a plurality of bright spots, projected on the flat surface 102. Disposing the grating 120 parallel to the flat surface 102 means, for example, disposing the grating 120 such that the plane including the axes of the respective optical fibers 121 of the FG element 122 constituting the grating 120 is parallel to the flat surface 102.

The grating 120 includes two FG elements 122. In this embodiment, the planes of the respective FG elements 122 are parallel to each other. Hereinafter, the planes of the respective FG elements 122 are referred to as "element plane." Also, in this embodiment, the axes of the optical fibers 121 of the two FG elements 122 are generally orthogonal to each other.

The FG element 122 is made up of several tens to several hundreds of optical fibers 121 having a diameter of about several tens of microns and a length of about 10 mm, arranged parallel in the shape of a sheet. The two FG elements 122 may be disposed in contact with each other, or in spaced relation with each other in the direction of the normal to their element planes. In the latter case, the two FG elements 122 are distanced from each other such that the projection of the pattern 11a will not be hindered. Typically, the laser beam L1 is perpendicular incident on the element plane of the grating 122.

As described above, in the projection device 11, the grating 120 including the two FG elements 122 as an optical system is used. Since it does not require a complicated optical system, the optical system casing can be downsized. Also, the projection device 11 can project the plurality of bright spots 11b as the pattern 11a on the target area with a simple construction using the grating 120. The pattern 11a includes a plurality of bright spots 11b, typically arranged in a square grid. The bright spots may be generally circular, and may be oval.

Figure 5:
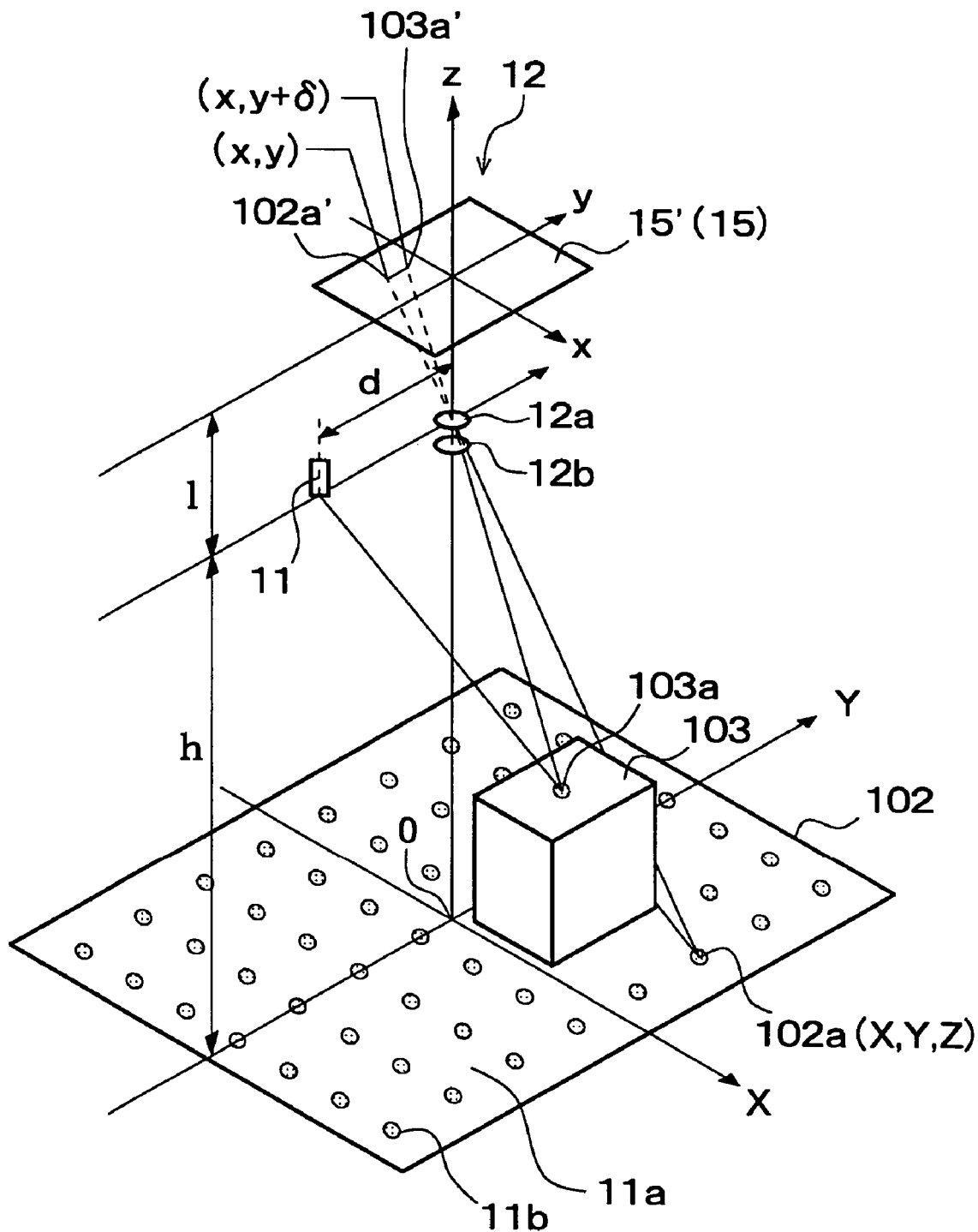
FIG. 5 is a conceptual perspective view illustrating the concept of shifts of bright spots according to the embodiment of the present invention.

Returning to FIG. 2, the image capturing apparatus 12 includes an imaging optical system 12a (see FIG. 5) and an image sensor device 15 (see FIG. 5). The image sensor device 15 is typically a CCD image sensor. Aside from CCDs, CMOS elements have been extensively released recently. The CMOS elements are also usable as the image sensor device 15, as a matter of course. Some CMOS elements themselves have the frame-to-frame subtraction and binarization functions, and the use of such CMOS elements are particularly preferable.

The image capturing apparatus 12 preferably includes a filter 12b (see FIG. 5) for attenuating light components not having wavelengths around that of the laser beam L1 generated by the light beam generation section 105 (see FIG. 3) described above. The filter 12b is typically an optical filter such as interference filter, and preferably disposed on the optical axis of the imaging optical system 12a. With this construction, the image capturing apparatus 12 can relatively increase the intensity of light of the pattern 11a projected by the projection device 11 out of the light received by the image sensor device 15, and hence can reduce the influence of ambient light. The laser beam L1 generated by the light beam generation section 105 is typically an infrared laser beam. The laser beam L1 may be irradiated continuously or intermittently. If the laser beam L1 is irradiated intermittently, the image capturing apparatus 12 performs the capturing an image in synchronization with the irradiations.

An example of installation of the FG sensor 10 is described. The projection device 11 and the image capturing apparatus 12 are disposed over the bed 3. In the drawing, the image capturing apparatus 12 is disposed generally over the head of the person 2, and the projection device 11 is disposed generally over the center of the bed 3. The projection device 11 projects the pattern 11a on the bed 3. The view angle of the image capturing apparatus 12 is set in such a manner as to capture an image of generally the center of the bed 3.

The projection device 11 is installed with its optical axis (projection direction of the laser beam L1) generally parallel to the vertical direction of the top of the bed 3, as shown in the drawing. The optical axis of the projection device 11 may be arranged generally parallel to the vertical direction of the top of the bed 3 as described above, but may be inclined with respect to the vertical direction.

Meanwhile, the image capturing apparatus 12 is installed with its optical axis inclined with respect to the vertical direction of the top of the bed 3. With this construction, the image capturing apparatus 12 and the projection device 11 can be easily installed as distanced from each other, for example. In other words, the baseline in triangulation can be easily made long. The optical axis of the image capturing apparatus 12 may be inclined with respect to the vertical direction of the top of the bed 3 as described above, but may be arranged generally parallel to the vertical direction as with the projection device 11. The projection device 11 and the image capturing apparatus 12 may be installed with their optical axes parallel to each other.

The projection device 11 and the image capturing apparatus 12 are preferably installed as distanced from each other. This increases the distance d (baseline length d) to be described later in relation to FIG. 5, and hence allows sensitive detection of changes. The baseline is preferably long, but may be short. In the latter case, small movements such as breaths are difficult to detect. However, detection of the gravity centers of the bright spots would allow detection of small movements (breaths).

Figure 4:
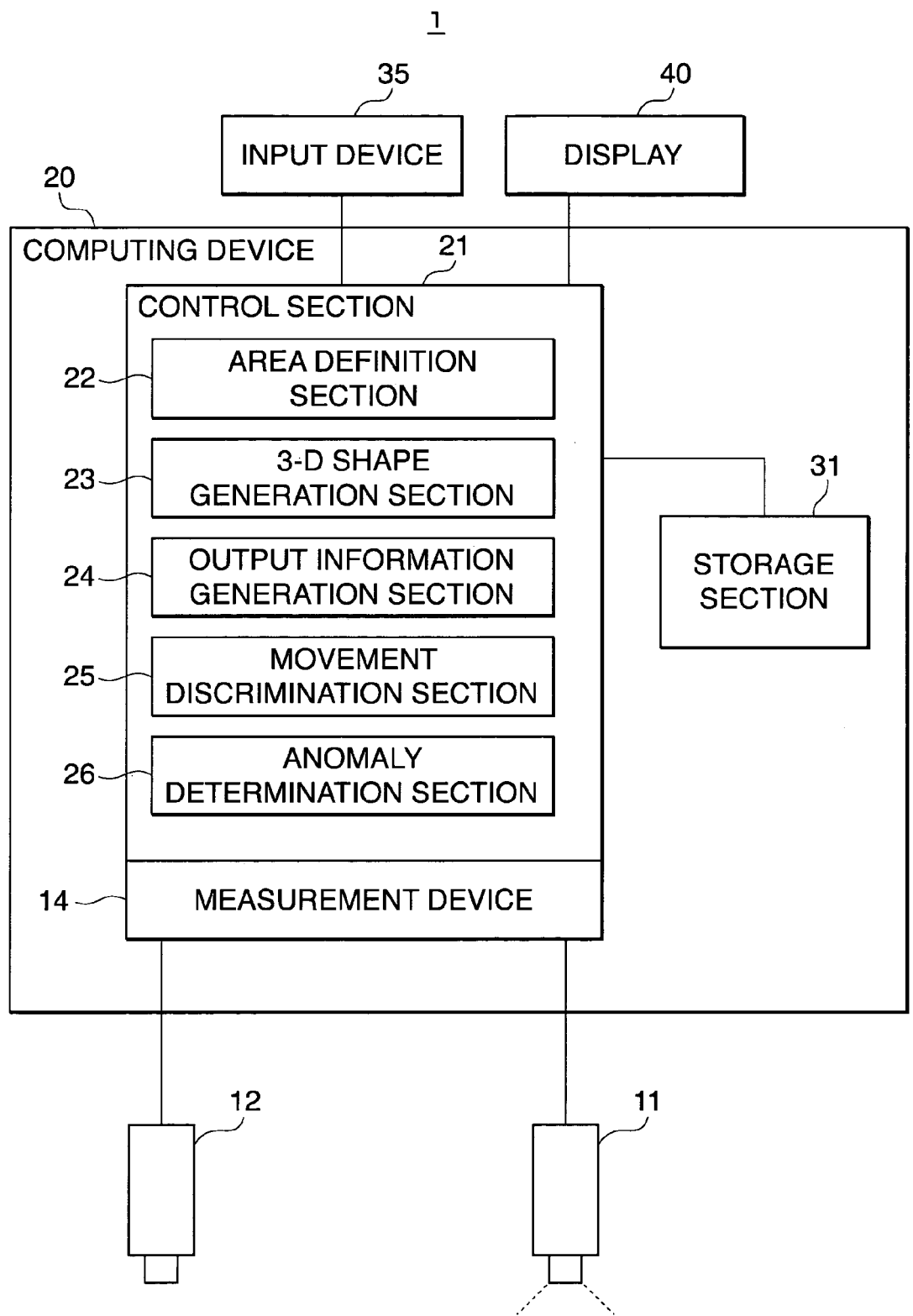
FIG. 4 is a block diagram showing an example of the construction of the monitoring apparatus according to the embodiment of the present invention.

With reference to the block diagram of FIG. 4, an example of the construction of the monitoring apparatus 1 is described. As described above, the computing device 20 is formed integrally with the measurement device 14. More specifically, the measurement device 14 is formed integrally with a control section 21 to be described later. The projection device 11 and the image capturing apparatus 12 are electrically connected to and hence controlled by the measurement device 14, as described above. In this embodiment, the computing device 20 is remotely located from the projection device 11 and the image capturing apparatus 12. More specifically, the computing device 20 may be installed beside the bed 3, in a room different from that where the bed 3 is placed such as nurse station, etc.

First of all, the measurement device 14 is described. As described above, the measurement device 14 measures shifts of the pattern on images captured by the image capturing apparatus 12, and measures sampling-point-moves in the height direction of the person 2 at a plurality of sampling points based on the shifts of the pattern measured. The measurement device 14 can acquire images captured by the image capturing apparatus 12. Also, the measurement device 14 measures shifts of the respective bright spots on the images captured by the image capturing apparatus 12. Here, the projected bright spots and the images of the bright spots on the captured images are simply referred to as "bright spots" for convenience. Measuring shifts of the bright spots refers to measuring the distances of the shifts of the bright spots (hereinafter referred to as "shift amounts").

Description is made in detail of the measurement of shifts of the bright spots by the measurement device 14. The measurement device 14 measures shifts of the bright spots based on images acquired at two different time points from the image capturing apparatus 12.

Description is made of the measurement of shifts of the bright spots based on the images at two different time points. The images at two different time points are preferably taken at and slightly before any time point. "Slightly before" means a sufficient time interval before the time point that allows detection of sampling-point-moves of the person 2. If it is desired to finely detect sampling-point-moves of the person 2, the time interval may be set short so that, for example, the person 2 cannot move greatly and substantially no movement can be detected, specifically 0.1 seconds or so, for example. Also, the time interval may be one to ten television cycles (1/30-1/3). If it is desired to roughly detect sampling-point-moves of the person 2, the time interval may be set long, specifically ten seconds or so, for example. If breaths of the person 2 are to be detected, as in this embodiment, too long a time interval such as one minute would hinder accurate detection of breaths and hence would not be appropriate. Hereinafter, the image acquired at any time point (present) is referred to as "acquired image" and that acquired slightly before the acquired image (past) is referred to as "reference image." The reference image is to be stored in a storage section 31. In this embodiment, the images at two different time points are an acquired image (N frame) and an image acquired one frame before it (N-1 frame). That is, the reference image is an image acquired one frame before the acquired image. The intervals of acquiring images may be appropriately determined depending, for example, on the processing speed of the apparatus or the type of movement desired to be detected as described above. The intervals may be, for example, 0.1 to 3 seconds, preferably about 0.1 to 0.5 seconds. Images may be acquired at shorter time intervals, in which case an averaging or filtering process may be performed to effectively reduce the influence of random noise, for example.

A waveform (for example, shift amount of the bright spots and sum total) obtained by measuring shifts of the bright spots based on images at two different time points, namely at and slightly before any time point, represents the differential of distance, or changes in speed. If it is desired to obtain a waveform representing changes in height, for example, the above-described waveform can be integrated into a waveform representing the distance, or changes in height.

The acquired image and the reference image, captured for example by the image capturing apparatus 12, include position information about the bright spots on the respective images. In other words, the acquired image and the reference image are images of the pattern 11a formed at respective time points by the projection device 11. In this embodiment, the reference image is stored in the storage section 31, not as a so-called image, but as position information, such as coordinates, about the respective bright spots, for example. This allows the process of measuring the shift amounts of the bright spots, which will be described later, to be achieved in a simple manner, by comparing the coordinates and directions of the bright spots, for example. The gravity centers of the bright spots are used as the positions thereof. This allows slight shifts of the bright spots to be measured.

The shift amounts of the bright spots are measured by comparing the position information about the respective bright spots on the reference image stored in the storage section 31 as described above with the position information about the respective bright spots on the acquired image. The respective shift amounts are obtained by counting the number of pixels by which the respective bright spots have moved (how many pixels they have moved), for example. The shift amounts of the bright spots measured may include the concept of the shifting directions of the bright spots. In other words, the shift amounts of the bright spots measured include information about the shifting directions. This can eliminate the need for generating a differential image as described later, thereby simplifying the process.

Aside from the above description where pieces of position information about the bright spots are compared, a differential image between the reference image and the acquired image may be created. In this case, the shift amounts of the bright spots are measured based on the positions of corresponding bright spots obtained from the differential image. Since only bright spots having moved remain on the differential image, the amount to be processed can be reduced.

The shift amounts of the bright spots measured by the measurement device 14 may be the moving averages or the period averages of the shift amounts of the bright spots, measured a specific number of times or within a specific period of time in the past. This can reduce random noise and unexpected noise such as by flicker of sunlight coming in through a window, and hence improve the accuracy of the shift amounts of the bright spots measured.

The measurement device 14 measures the shift amount of each bright spot constituting the pattern 11a as described above. That is, the plurality of bright spots correspond in position to the plurality of sampling points. The measurement device 14 outputs, to the control section 21, the shifts measured, or the shift amounts measured, of the respective bright spots constituting the pattern 11a, as the measurement results. That is, the measurement results represent the shift amounts of the bright spots measured based on the images at two different time points. The measurement results correspond to the sampling-point-moves in the height direction of the object, namely the person 2, at the respective bright spots (sampling points), as described later in relation to FIG. 5. Hereinafter, the measurement results are referred to as "movement information." The measurement device 14 outputs the measurement results at the respective sampling points as movement information. The sampling-point-moves in the height direction of the person 2 include sampling-point-moves associated with breaths of the person 2, for example.

With reference to the conceptual perspective view of FIG. 5, the concept of the shifts of the bright spots is described. In this description, a flat surface 102 and a solid 103 are used as the target area and the object, respectively, for simplicity. Also, in this description, an image of the pattern 11a without the solid 103 on the flat surface 102 and that with the solid 103 on the flat surface 102 are used as the reference image and the acquired image, respectively, for illustration purposes.

In the drawing, the solid 103 is placed on the flat surface 102. An orthogonal coordinate system X-Y-Z is positioned with its X- and Y-axes in the flat surface 102. The solid 103 is placed in the first quadrant in the X-Y coordinate system. Meanwhile, in the drawing, the projection device 11 and the image capturing apparatus 12 are disposed above the flat surface 102 in the Z-axis direction. The image capturing apparatus 12 captures an image of the flat surface 102 while the pattern 11a is projected thereon by the projection device 11. In other words, the image capturing apparatus 12 captures an image of the solid 103 placed on the flat surface 102.

An imaging lens 12a as an imaging optical system of the image capturing apparatus 12 is disposed with its optical axis coincided with the Z-axis. The imaging lens 12a forms an image of the pattern 11a, either on the flat surface 102 or on the solid 103, on an image plane 15' of the image sensor device 15 of the image capturing apparatus 12. The image plane 15' is typically a plane perpendicular to the Z-axis. An x-y orthogonal coordinate system is positioned in the image plane 15' such that the Z-axis passes through the origin of the x-y coordinate system. The projection device 11 is disposed distanced from the flat surface 102 as much as the imaging lens 12a is and distanced from the imaging lens 12a by the distance d (baseline length d) in the negative direction of the Y-axis. The projection device 11 projects the pattern 11a made up of the plurality of bright spots 11b on the solid 103 and the flat surface 102. The direction of the y-axis is also the direction of the baseline in triangulation.

The pattern 11a projected toward the flat surface 102 by the projection device 11 is blocked by the solid 103 and thus does not reach the flat surface 102 in a region where the solid 103 is present. Thus, a bright spot 11b, which would be projected at a point 102a on the flat surface 102 without the solid 103, is projected at a point 103a on the solid 103. Because the bright spot 11b has moved from the point 102a to the point 103a and the imaging lens 12a and the projection device 11 are distanced from each other by the distance d (baseline length d), the bright spot 11b is imaged on the image plane 15', not at a point 102a' (x, y) where it should be without the solid 103, but at a point 103a' (x, y+δ). In other words, comparing the time point with the solid 103 with the time point without the solid 103, the image of the bright spot 11b moves in the y-axis direction by the distance δ.

Figure 6:
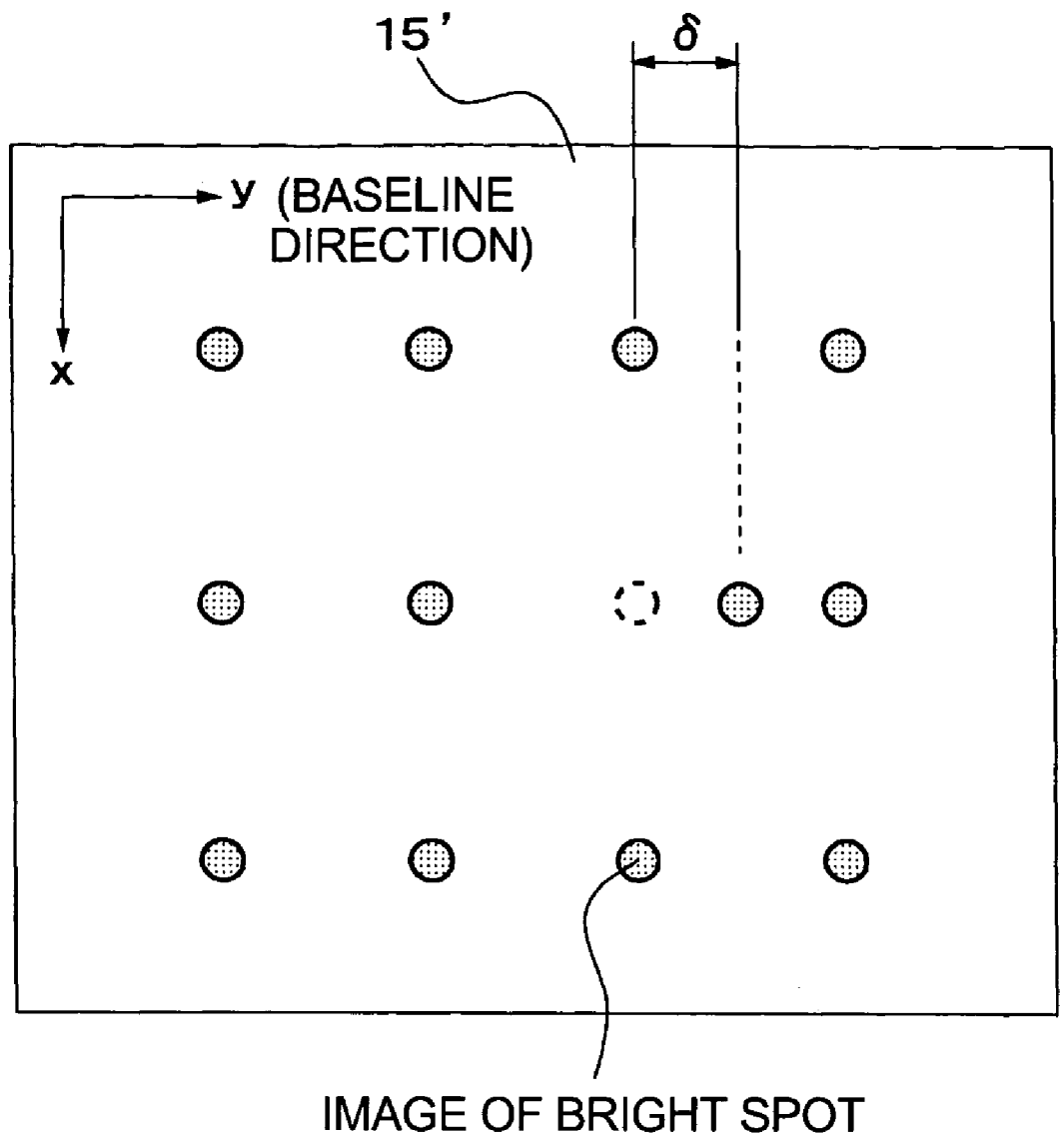
FIG. 6 is a schematic view illustrating the bright spots imaged on an image plane of FIG. 5.

That is, as shown for example in FIG. 6, the bright spot imaged on the image plane 15' of the image sensor device 15 has moved in the y-axis direction by the distance δ because of the presence of the solid 103 with a height.

Thus, the point 103a on the solid 103 can be located 3-Dimensionally by measuring the shift amount δ of the bright spot. In other words, the height of the point 103a, for example, can be known. Thus, by measuring the difference between positions on the image plane 15' where certain points would be imaged without the solid 103 and the actual positions imaged on the image plane 15', the distribution of heights, or 3-D shape, of the solid 103 can be measured. In other words, 3-D coordinates of the solid 103 can be measured. Also, by reducing the pitch of the pattern 11a, or the pitch between the bright spots 11b, to a degree which does not obscure the correspondence of the bright spots 11b, the distribution of heights of the solid 103 can be precisely measured accordingly.

Based on the concept as described above, the measurement device 14 can measure the heights of the object by measuring the shift amounts of the bright spots. In this description, however, sampling-point-moves in the height direction are measured based on the acquired image and the image acquired one frame before the acquired image, or the reference image, to monitor the amounts of changes in shifts of the bright spots. Since the object is to detect sampling-point-moves in the height direction of the person 2, the fact that the absolute heights of the person 2 cannot be measured, for example, does not cause a problem.

Returning to FIG. 4, the computing device 20 is described. The computing device 20 includes a control section 21 for controlling the monitoring apparatus 1. The control section 21 is connected to a storage section 31. Preferably, the storage section 31 chronologically stores images acquired from the image capturing apparatus 12. The storage section 31 can also store data such as calculated information.

The control section 21 is connected to a display 40 as information output means for outputting information of an area including an area defined by an area definition section 22 to be described later. The display 40 is typically an LCD. The display 40 outputs, by displaying, information of an area including the area defined by the area definition section 22. The information of an area including the area defined by the area definition section 22 includes, for example, the presence or absence of areas with sampling-point-moves in difference phases to be described later, the sizes and positions of areas in the same phase, and, in a case where breaths are to be detected as in this embodiment, waveforms representing sampling-point-moves in respective areas of the person 2 and the amplitudes thereof. In this embodiment, the information of an area including the area defined by the area definition section 22 is analysis information to be described later.

The control section 21 is also connected to an input device 35 for inputting information for operating the monitoring apparatus 1. The input device 35 is a touch panel, a keyboard, or a mouse, for example. The input device 35 is externally connected to the computing device 20 in the drawing, but may be built therein.

Further, the control section 21 includes therein an area definition section 22 as area definition means for defining an area where a plurality of the sampling-point-moves measured by the measurement device 14 are in the generally same phase, and an output information generation section 24 for generating analysis information of an area including the area defined by the area definition section 22. The control section 21 further includes therein a 3-D shape generation section 23 as shape information generation means for generating shape information allowing recognition of the shape of the person 2. In this description, the output information generation section 24 generates analysis information for displaying the area defined by the area definition section 22 over the shape information generated by the 3-D shape generation section 23. The respective components are described in detail below.

The area definition section 22 defines an area where sampling-point-moves at a plurality of the sampling points are in the generally same phase based on the movement information, or the measurement results by the measurement device 14. In this description, the term "phase" may include the concept of the direction of a movement, and "the generally same phase" (hereinafter simply referred to as "the same phase") may include the simple concept that the directions of sampling-point-moves are coincident. Also, in this description, the area definition section 22 distinguishes sampling-point-moves in the same phase depending on whether the sampling-point-moves measured at the respective sampling points by the measurement device 14 are upward sampling-point-moves or downward sampling-point-moves. That is, an area in the same phase is made up of sampling points in the same phase distinguished.

If a specific number or more of the sampling points in a specific area represent sampling-point-moves in the same, specific type of phase, the area definition section 22 defines the specific area as an area where the sampling-point-moves in the specific type of phase are occurring. The specific value may be, for example, about $\frac{1}{5}$ to $\frac{1}{20}$ the number of the sampling points existing in the specific area, preferably about $\frac{1}{10}$ that number (value).

As a specific example, the area definition section 22 first determines the phase of movement desired to define into areas. In this example, an area in the upward phase is first to be defined. As described above, the bright spots respectively correspond to the sampling points. Then, one of the sampling points is focused. If the shift amount of the bright spot corresponding to the measurement point in focus is the specific value or larger and the phase of the movement of the person 2 at the measurement point is upward, the area including the measurement point is set as a search area as the specific area. The search area may be sized to include about 9 to 25 sampling points, for example. The specific value is a first threshold value Th1 to be described later.

If the search area includes a specific number or more sampling points corresponding to bright spots with a shift amount of the first threshold value Th1 or larger and a movement in the upward phase, the specific search area is defined and labeled as an area with upward sampling-point-moves. Then, another measurement point outside the search area is focused and subjected to the same process as described above. This is repeated until there is no measurement point to be focused. In other words, the process is repeated until all the sampling points are checked whether their corresponding bright spots have a shift amount of the specific value or larger and a movement in the upward phase. As a result, if there are a plurality of adjacent, labeled search areas, the adjacent search areas are joined and labeled again. Once the process for sampling-point-moves of the person 2 in the upward phase is finished as described above, the same process is performed for sampling-point-moves of the person 2 in the downward phase. In this manner, the area definition section 22 defines areas with upward sampling-point-moves and those with downward sampling-point-moves on the person 2. That is, both/either areas with sampling-point-moves in the upward phase and/or those with sampling-point-moves in the downward phase can be defined. Defining areas with sampling-point-moves in the same phase using the area definition section 22 as described above allows one to know which part of the body of the person 2 is moving upward or downward.

The area definition section 22 may search a specific area for sampling points representing sampling-point-moves in the same, specific type of phase, form a group of sampling points representing the sampling-point-moves in the generally same phase based on the search results, and define the thus formed group of sampling points as an area where the sampling-point-moves in the generally same phase are occurring.

As a specific example of this case, first of all, the area definition section 22 determines the phase of sampling-point-moves desired to define into an area in the same manner as described above. This example will first define an area including sampling-point-moves in the upward phase. Then, one of the sampling points is focused. The area including the measurement point in focus is set as a search area as the specific area. In this example, the search area may be sized to include several, about 4 to 9, sampling points. Then, a search is made in the search area for a measurement point with a movement in the upward phase.

If there is found any measurement point with a movement in the upward phase in the search area, the measurement point is labeled in the same manner as the measurement point in focus, designated as a new measurement point in focus, and used to set a new search area. Again, a search is made in the new search area for a measurement point with a movement in the upward phase. The found measurement point, if any, is labeled in the same manner. If no measurement point with a movement in the upward phase is found, the search is ended. However, if there are found a plurality of sampling points with sampling-point-moves in the upward phase in a search area, each measurement point is designated as a new measurement point in focus and used to set a new search area. Repeating the process of setting a search area, making a search for a measurement point with a movement in the upward phase, and labeling the found measurement point forms a group of sampling points with sampling-point-moves in the upward phase.

Then, a measurement point which has not been focused yet or is not included in any group of sampling points is designated as a measurement point in focus and labeled in the same manner. At this time, the labeling is performed differently for distinction from the former group (for example, the label is changed). The above process is repeated. When there is no measurement point which has not been focused yet or is not included in any group of sampling points formed, the search for sampling points with sampling-point-moves in the upward phase is finished. In other words, the labeling is finished. The thus formed groups of sampling points are defined as areas with sampling-point-moves in the upward phase. Among the thus formed groups of sampling points, the group including the largest number of sampling points may be defined as an area with sampling-point-moves in the upward phase. The same process can be performed for sampling-point-moves in the downward phase to form areas with sampling-point-moves in the same phase. That is, both/either an area with sampling-point-moves in the upward phase and/or that with sampling-point-moves in the downward phase can be defined.

The area definition section 22 can further compute to define a boundary where the phases of sampling-point-moves reverse based on the defined areas. The boundary may be computed to define in a case where both an area with upward sampling-point-moves and that with downward sampling-point-moves are defined on the person 2 in the definition of areas described above. The computation to define a boundary is described specifically below. Here, the boundary is described as a line. That is, the area definition section 22 computes to define a boundary line.

First of all, the area definition section 22 distinguishes an area including the largest number of sampling points with sampling-point-moves in the same, specific type of phase, or in the same phase, from the areas defined as described above. The area with the largest number is distinguished for each phase. That is, in this description, the area with the largest number is distinguished for sampling-point-moves in the upward phase and in the downward phase respectively. Then, the average coordinate of the sampling points in the distinguished area with the largest number is calculated. The calculation is performed for each distinguished area with the largest number, that is, the areas with sampling-point-moves in the upward phase and in the downward phase respectively. Then, the middle point between the calculated average coordinates is calculated and designated as a boundary point. In this description, the straight line passing through the boundary point and perpendicular to the baseline direction in FIG. 2 is designated as the boundary line. The boundary line is used as a boundary line between the abdomen and the thorax of the person 2 in the discrimination of movement to be described later.

The average coordinate may be a coordinate of the center of gravity weighted by the shift amounts of the bright spots, for example. In this case, the average coordinate can be calculated by multiplying the coordinate value of each bright spot by the shift amount of that bright spot in the coordinate axis direction, and adding together the multiplied values for the bright spots belonging to the area, and dividing the obtained sum by the sum of the shift amounts of the bright spots. The boundary point may not be the middle point between the average coordinates, but may be calculated in consideration of the size of each area, the number of the bright points and the sum of the shift amounts of the bright spots in each area, and the like. For example, the boundary point may be a point internally dividing the line between the average points at the ratio of, or at the inverse ratio of, the sum of the shift amounts of the bright spots in each area. The boundary line may be a straight line perpendicular to the straight line connecting the average coordinates, or may not be a straight line but may be set according to the shapes of the respective areas.

The 3-D shape generation section 23 generates shape information allowing recognition of the shape of the person 2 as described above. The shape information generated by the 3-D shape generation section 23 may be, for example, an image representing the 3-D shape of the person 2, or simply a captured image of the person 2. It also may be an image showing the schematic external shape of the body of the person 2. In this embodiment, the shape information is an image showing the 3-D shape (hereinafter simply referred to as "3-D shape").

Figure 7:
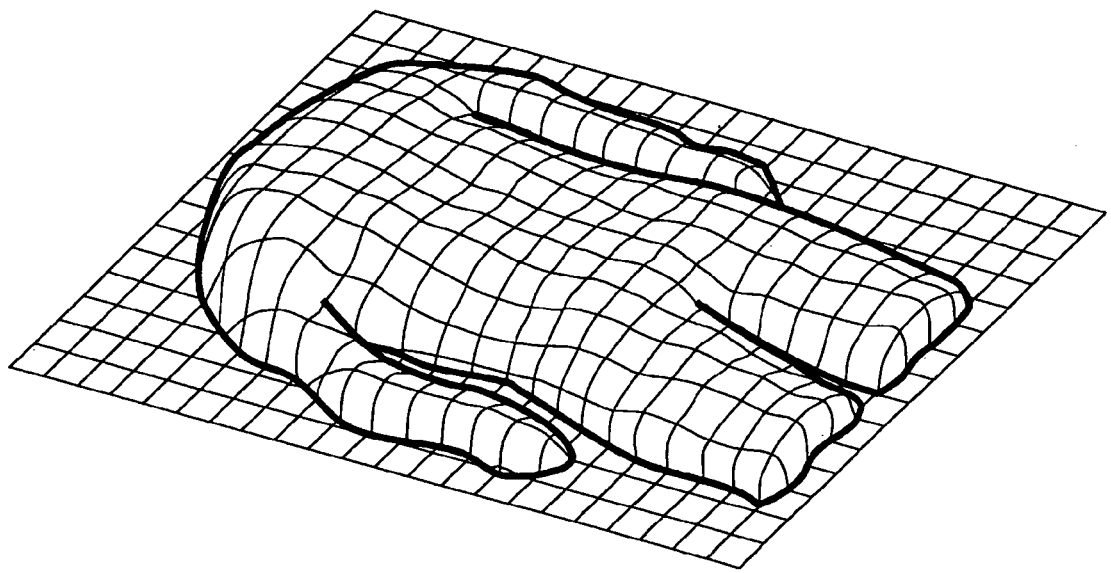
FIG. 7 is a schematic view illustrating a 3-D shape generated by a 3-D shape generation section according to the embodiment of the present invention.

FIG. 7 shows an example of the 3-D shape. The 3-D shape shown in the drawing is an image as displayed on the display 40.

The 3-D shape generation section 23 may generate the 3-D shape as described above based on the measurement results by the measurement device 14 of the FG sensor 10. In this case, the measurement device 14 uses an image at any time point (present) and that at a time point when the person 2 is not on the bed 3 as the two images at two different time points in the measurement of the shift amounts of the bright spots. The measurement device 14 then outputs the measurement results at the respective sampling points measured based on the images at two different time points as height information. Then, the 3-D shape generation section 23 generates a 3-D shape based on the height information, or the measurement results by the measurement device 14.

The height information or the measurement results by the measurement device 14, which correspond to the heights of the person 2 at the plurality of sampling points, can further be used to calculate the actual heights. In this case, the heights of the person 2 at the respective sampling points can be calculated by triangulation, based on the height information or the shift amounts of the bright spots at the respective sampling points. More precisely, the heights from the top of the bed 3 can be calculated.

Specifically, with the distance between the projection device 11 and the image capturing apparatus 12 (baseline length) being "d," the focal length of the imaging lens 12a being "l," the distance from the imaging lens 12a to the top surface of the bed 3 being "h," and the shift amount of the bright spot being "67," for example, the height can be calculated by the following equation (1):

$$Z=(h^2 \cdot \delta)/(d \cdot 1 + h \cdot \delta) \quad (1)$$

In this case, since the sampling points are arranged in spaced relation, the heights of the person 2 at locations between the sampling points cannot be known. Thus, the external shape of the person 2 would be difficult to grasp if the 3-D shape is generated using the bare heights of the person 2 at the respective sampling points calculated. For the purpose of supplementation, the 3-D shape generation section 23 performs interpolation for a part of the person 2 where necessary. Positioning the thus obtained heights of the person 2 on a coordinate system can generate a 3-D shape as shown in FIG. 7, for example.

Next, description is made of the output information generation section 24. The output information generation section 24 generates analysis information for displaying the areas defined by the area definition section 22 over the shape information, or in this description the 3-D shape, generated by the 3-D shape generation section 23. The generated analysis information is outputted to and displayed on the display 40. The output information generation section 24 generates, as the analysis information, an image where the areas defined by the area definition section 22 are superimposed on the 3-D shape such that their corresponding coordinates (positions) coincide. Determination results by an anomaly determination section 26 to be described later are also included in the generated analysis information.

Figure 8:
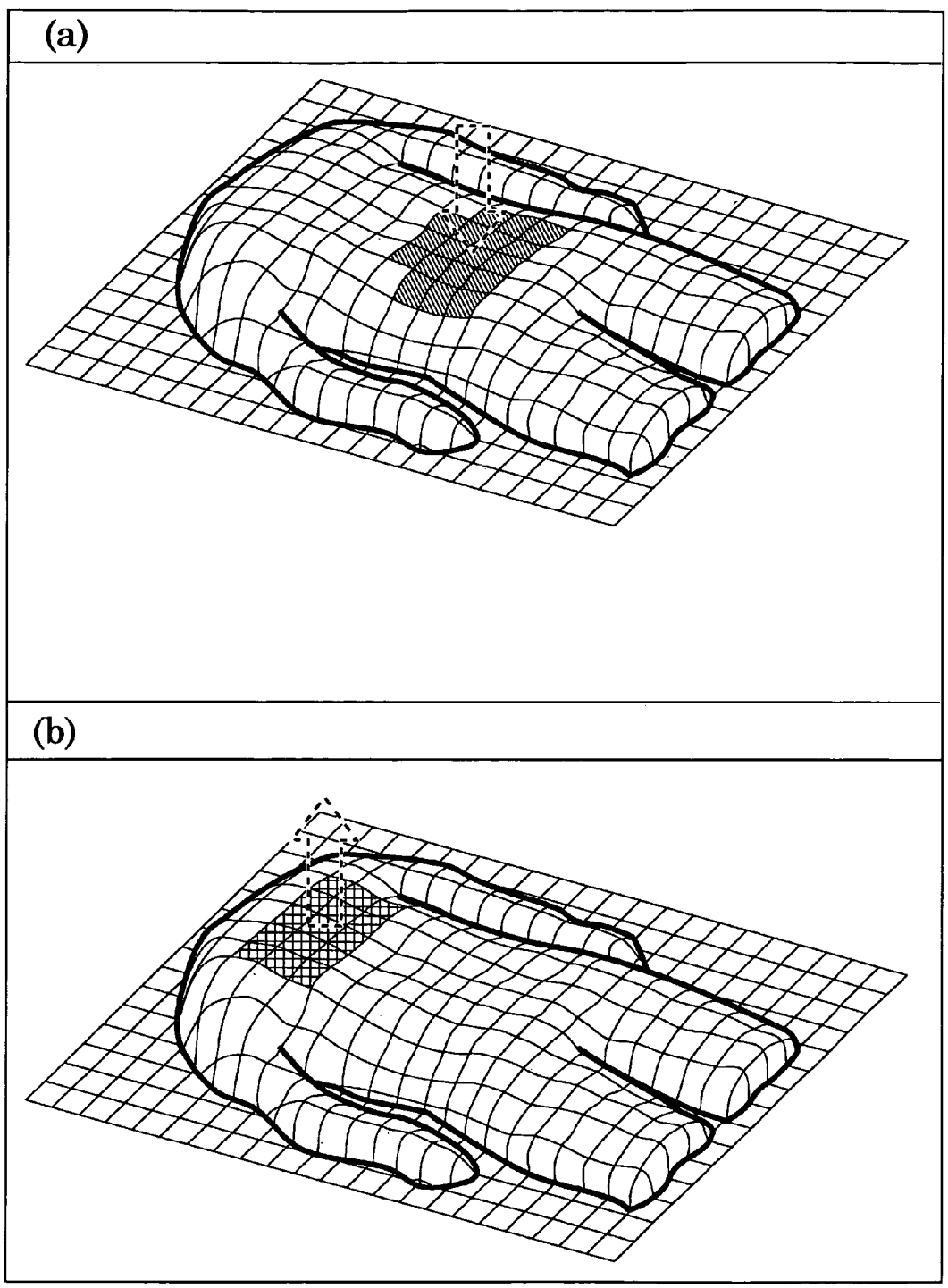
FIG. 8 is a schematic view of areas defined by the area definition section superimposed on the 3-D shape of FIG. 7. where

With reference to the schematic view of FIG. 8, description is made of an example of display where the defined areas are superimposed on the 3-D shape, or in other words an example of the generated analysis information. For illustration purposes, the example of the generated analysis information is shown as an image as displayed on the display 40. As shown in the drawing, the areas defined by the area definition section 22 are superimposed on the 3-D shape as described in relation to FIG. 7 such that their corresponding points coincide. The defined areas are superimposed on the 3-D shape so that the phases of the sampling-point-moves in the defined areas can be distinguished. FIG. 8(*a*) shows a case where the abdomen of the person 2 is moving downward, more specifically exhalation in abdominal breathing. Meanwhile, FIG. 8(*b*) shows a case where the thorax of the person 2 is moving upward, more specifically inhalation in thoracic breathing.

The area with movement in the upward phase and that with movement in the downward phase are applied with different patterns in this example, but may be colored differently (for example, blue upward and red downward). The phase of movement may be indicated by an arrow (shown by the broken line in the drawing), for example. This facilitates recognition of which part of the body of the person 2 is moving upward or downward. In this case, also, displaying patterns with different color depths or intervals or arrows with different widths or lengths further facilitates recognition of the changes in the sampling-point-moves. Data representing changes in the heights, obtainable by integrating the changes in the sampling-point-moves, may also be processed in the same manner. For example, a part with an increasing height may be displayed in a brighter color or indicated by a longer arrow, reflecting the amount of increase, to facilitate easy recognition of the changes in the heights.

Figure 9:
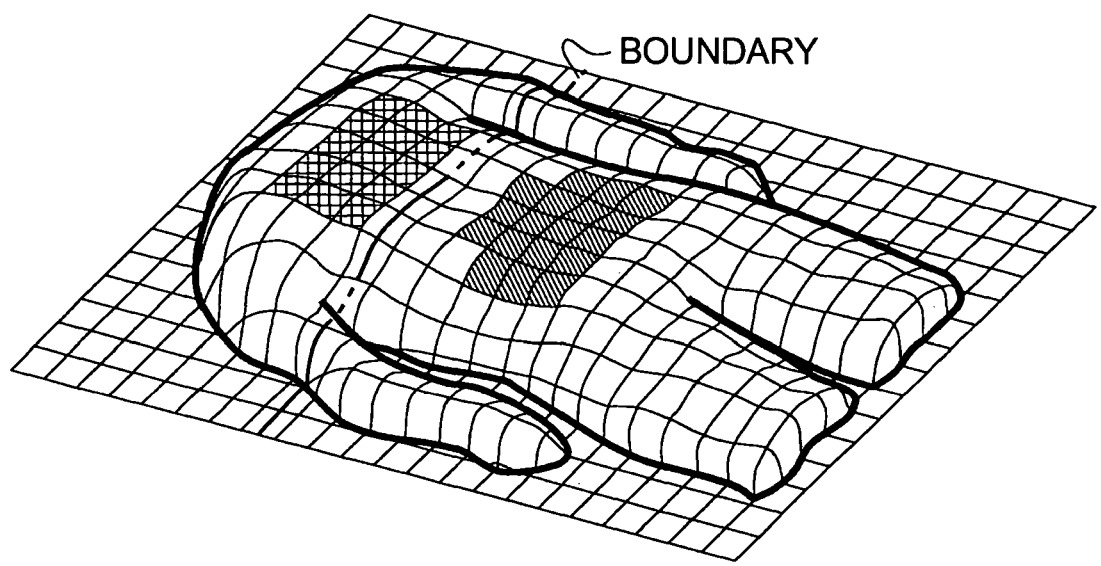
FIG. 9 is a schematic view of areas defined by the area definition section superimposed on the 3-D shape of FIG. 7, with a boundary computed to define by the area definition section.

Further, as shown in the schematic view of FIG. 9, the boundary, if computed to define by the area definition section 22, can be superimposed on the 3-D shape in the generation of the analysis information. The boundary is shown as a boundary line. This facilitates recognition of the boundary between the thorax and the abdomen of the person 2, for example. This is advantageous in diagnosing sleep apnea syndrome to be described later.

The monitoring apparatus 1 displays the areas defined by the area definition section 22 over the 3-D shape on the display 40 by displaying the thus generated analysis information.

The shape information is an image representing the 3-D shape of the person 2, for example. However, the shape information may be relatively simple and may be, for example, an illustration showing the schematic external shape of a body printed on a film. In this case, with the film placed over the screen of the display 40, the display 40 can display the defined areas over the shape information. In this case, also, the 3-D shape generation section 23 is not necessary, and the output information generation section 24 generates analysis information for displaying the areas defined by the area definition section 22 over the illustration showing the schematic external shape of the body printed on the film.

Returning to FIG. 4, the control section 21 further includes therein a movement discrimination section 25 for discriminating the type of the sampling-point-moves of the person 2 based on the areas defined by the area definition section 22. The movement discrimination section 25 discriminates the type of the sampling-point-moves of the person 2 also based on the sampling-point-moves in the height direction of the person 2 measured at the plurality of sampling points by the measurement device 14 of the FG sensor 10. In other words, the movement discrimination section 25 discriminates the type of the sampling-point-moves of the person 2 based on the movement information outputted by the measurement device 14. The type of the sampling-point-moves of the person 2 discriminatable by the movement discrimination section 25 typically includes breathing, bodily movement, and immobility (without movement). That is, the movement discrimination section 25 can detect breaths of the person 2 based on the areas defined by the area definition section 22 and the sampling-point-moves in the height direction of the person 2 measured at the plurality of sampling points by the measurement device 14. The bodily movement, which indicates movements of the body of the person 2, broadly includes the concept of not only movements such as standing up and sitting down, but also general movements of the limbs The movement discrimination section 25 discriminates the sampling-point-moves of the person 2 in the respective areas defined by the area definition section 22. Specifically, the movement discrimination section 25 calculates the average of the shift amounts of the bright spots at the sampling points in the respective areas defined by the area definition section 22 based on the movement information outputted by the measurement device 14. The movement discrimination section 25 discriminates the sampling-point-moves of the person 2 as motionless if the absolute value of the average is smaller than a first threshold Th1, as breathing if the absolute value is not smaller than the first threshold Th1 but smaller than a second threshold Th2, and as bodily movement if the average is not less than the second threshold Th2. The first threshold is smaller than the second threshold. The first and second thresholds Th1 and Th2 are preferably set such that the range between them includes the shift amounts of the bright spots corresponding to the amplitude of breaths of the person 2. For example, the first and second thresholds may be set to the shift amounts of the bright spots corresponding to height changes of the person 2 of about 1 mm and about 20 mm, respectively.

If the movement discrimination section 25 discriminates the person 2 as breathing, the movement discrimination section 25 preferably detects the breaths of the person 2. The movement discrimination section 25 may detect the breaths by comparison with specific upper and lower limit thresholds set for both or either the amplitude and/or the period (frequency) of periodic changes of the average over time. The upper and lower limit thresholds for the period are preferably set, for example, to a range including the period of breaths of the person, for example 5 cycles per minute for the lower limit and 60 cycles per minute for the upper limit. The number of breaths is in the range of five to thirty per minute for an adult, and tends to be larger for an infant. The upper and lower limits for the amplitude are respectively set to the second threshold Th2 and the first threshold Th1. The thus detected breaths of the person 2 form a waveform pattern.

Figure 10:
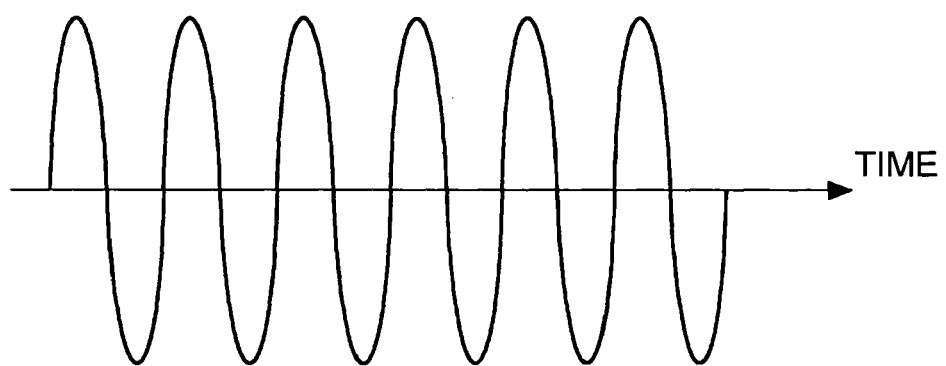
FIG. 10 is a graph of a waveform pattern representing breaths according to the embodiment of the present invention.

FIG. 10 shows an example of the waveform pattern representing the breaths.

Further, the movement discrimination section 25 preferably detects the number of the breaths. The number of the breaths can be detected by data processing, such as Fourier transform, of changes over time of the sum of the shift amounts of the bright spots in the areas where the movements are discriminated as breaths.

The control section 21 further includes therein an anomaly determination section 26 for determining an anomaly of the person 2 based on the sampling-point-moves in the height direction of the person 2 measured by the measurement device 14. More specifically, the anomaly determination section 26 determines an anomaly of the person 2 based on the detection results of the breaths of the person 2 by the movement discrimination section 25. The anomaly determination section 26 also serves as anomaly determination means for determining an anomaly of the person 2 based on the areas defined by the area definition section 22. In this description, determining an anomaly of the person 2 means determining whether or not the person 2 is in a critical condition.

Preferably, the anomaly determination section 26 determines that the person 2 is in a critical condition based on the following determination criteria. For example, in a case where the period of the breathing pattern has been disturbed over a short time or changed abruptly while the movement discrimination section 25 is detecting breaths, the person 2 is determined to be in a critical condition since lung diseases such as spontaneous pneumothorax and bronchial asthma, heart diseases such as congestive heart failure, and cerebrovascular diseases such as cerebral hemorrhage are suspected. In a case where the breathing pattern is missing for an extended time, the person 2 is determined to be in a critical state since the person 2 is suspected to have stopped breathing. In a case where frequent bodily motions, not breaths, of the person 2 occur over a short time, the person 2 is determined to be in a critical condition since the person 2 is suspected to be struggling in agony for some reason.

Figure 11:
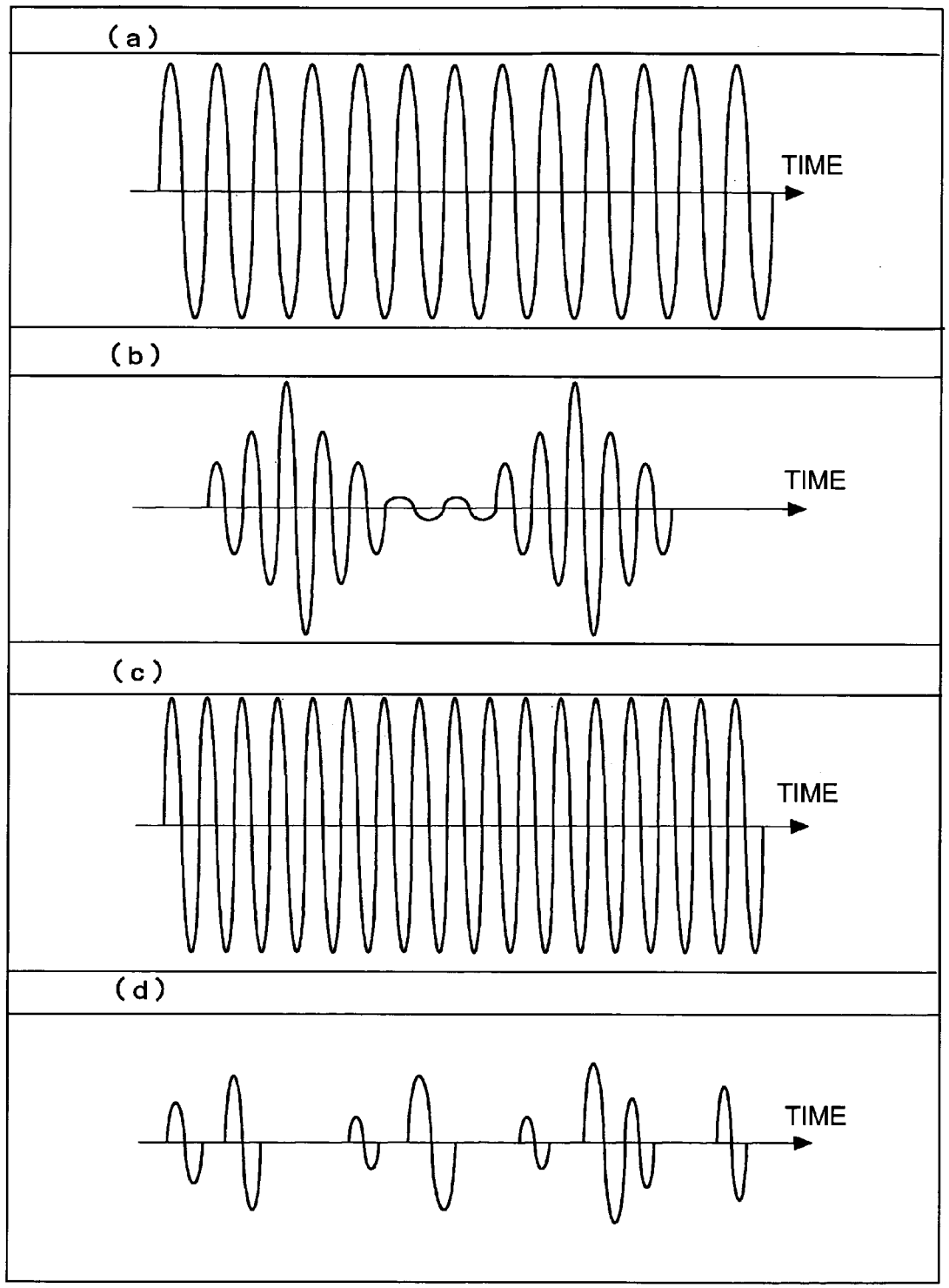
FIG. 11 is graphs of waveform patterns of the type of FIG. 10, representing normal and abnormal breaths.

With reference to FIG. 11, examples of normal and abnormal breathing patterns are described. FIG. 11(a) shows the normal, periodic breathing pattern. For an adult, the number of breaths per minute normally ranges about 10 to 20. The abnormal breathing patterns include those considered to occur when a physiological disorder, such as Cheyne-Stokes breathing, central hyperventilation, ataxic breathing, and Kussmaul breathing, is occurring in the body.

FIGS. 11(b), 11(c), and 11(d) respectively show breathing patterns of the Cheyne-Stokes breathing, the central hyperventilation, and the ataxic breathing.

FIG. 12 shows the names of diseases and the diseased locations in the cases of the abnormal breathing patterns described above.

Preferably, the anomaly determination section 26 utilizes the fact that the frequency, number of appearances, and depth of the breaths of the respective breathing patterns are different to discriminate which breathing pattern the person 2 is following and determine whether or not the person 2 is in a critical condition. The breathing patterns such as described above are preferably stored in the storage section 31. This facilitates the determination of whether or not the person 2 is breathing normally by comparison with the stored patterns.

The anomaly determination section 26 further determines that the person 2 is breathing abnormally and hence in a critical condition in a case where the person 2 is determined to be breathing in a breathing pattern considered to occur when a physiological disorder is occurring in the body. The breathing patterns considered to occur when a physiological disorder is occurring in the body include those described in relation to FIG. 11, for example. The thus determined critical condition of the person 2 is preferably outputted by the control section 21 to an output device 36 or an alarming device (not shown in the drawing), for example. The information to be outputted includes, for example, the number (period) of the breaths or the frequency of the sampling-point-moves detected of the person 2, the name of the abnormal breathing pattern, the name of a possible disease causing the breaths, and the diseased organ and location.

The anomaly determination section 26 determines an anomaly of the person 2 also based on the phases of the respective areas defined by the area definition section 22. Specifically, in a case where both an area with upward sampling-point-moves and that with downward sampling-point-moves are defined on the person 2 by the area definition section 22, the anomaly determination section 26 determines an anomaly of the person 2 based on the sampling-point-moves of the person 2 in the respective areas. This allows determination of sleep apnea syndrome to be described below.

The sleep apnea syndrome is described here. The sleep apnea syndrome (SAS) is defined as a disease causing one to frequently stop breathing during sleep and involving 30 times or more of breathless periods of 10 seconds or longer during one night's sleep (7 hours) or 5 times or more of breathless periods during one hour of sleep. The sleep apnea syndrome is classified into three types.

A first type is obstructive sleep apnea syndrome (OSAS) in which the pleuroperitoneum is performing breathing movements but nasal and oral airflows are blocked in the choked upper airway, or in other words attempts are made to breathe while no breath is occurring. For most patients, the sleep apnea syndrome is said to be obstructive. The obstructive sleep apnea syndrome is often complicated by obesity, cerebrovascular disorder, arrhythmia, respiratory failure, or high blood pressure.

A second type is central sleep apnea syndrome (CSAS) in which not only airflows but also motions of the pleuroperitoneum or breathing motions themselves stop. The central sleep apnea syndrome is often observed with patients of an encephalopathy or a circulatory disease, and complicated seriously less often than cases with the obstructive sleep apnea syndrome. A third type is mixed sleep apnea syndrome which starts as central apnea and then shifts to obstructive apnea.

Figure 13:
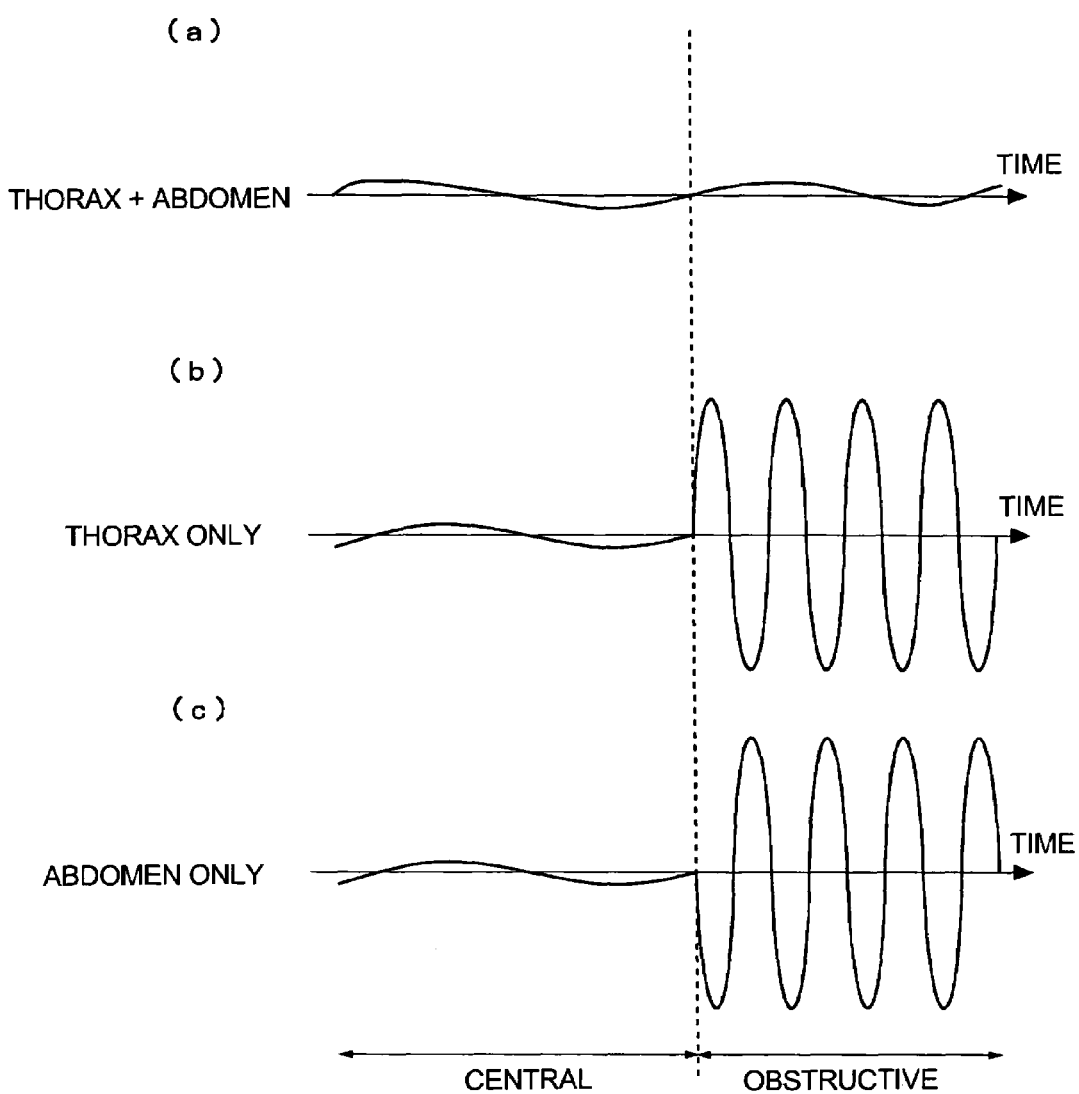
FIG. 13 is graphs of waveform patterns of the type of FIG. 10. representing breaths of sleep apnea syndrome.

FIG. 13 shows examples of breathing patterns of the obstructive sleep apnea syndrome and the central sleep apnea syndrome.

As shown in FIG. 13, in the obstructive sleep apnea syndrome, the choked throat does not allow airflows to pass in spite of attempts to breathe. Thus, the abdomen and the thorax move in generally opposite phases (see FIG. 13(*b*) and FIG. 13(*c*)). For example, the abdomen moves upward while the thorax moves downward. This phenomenon is not observed with the central apnea. Thus, the abdominal area and the thoracic area are automatically distinguished from each other according to the boundary computed to define by the area definition section 22 to detect breaths in the respective divided areas. If both the thorax and the abdomen were considered as one measurement area when the obstructive apnea is occurring, the thorax and the abdomen move oppositely and almost no movement would be detected, with the detected breathing patterns in the respective areas of the person 2 canceling each other (see FIG. 13(*a*)). In the manner of this description, the breathless state (immobility) determined by the anomaly determination section 26 can be further discriminated as obstructive or central.

The anomaly determination section 26 determines as normal if overall motions in a single phase, more specifically breaths in a single phase, are detected, and as abnormal in central apnea if no overall motion is detected (immobility is determined). If breaths in opposite phases are detected in the thorax and the abdomen, the anomaly determination section 26 determines as abnormal in obstructive apnea.

The above determination results with the anomaly determination section 26 is made to be displayed on the display 40. The anomaly determination section 26 outputs the determination results to the output information generation section 24. In this case, the output information generation section 24 generates and outputs analysis information including the determination results to the display 40. In this way, as the determination results produced with the anomaly determination section 26 are displayed on the display 40, for example a measurement operator can easily recognize anomaly of the person 2.

Figure 14:
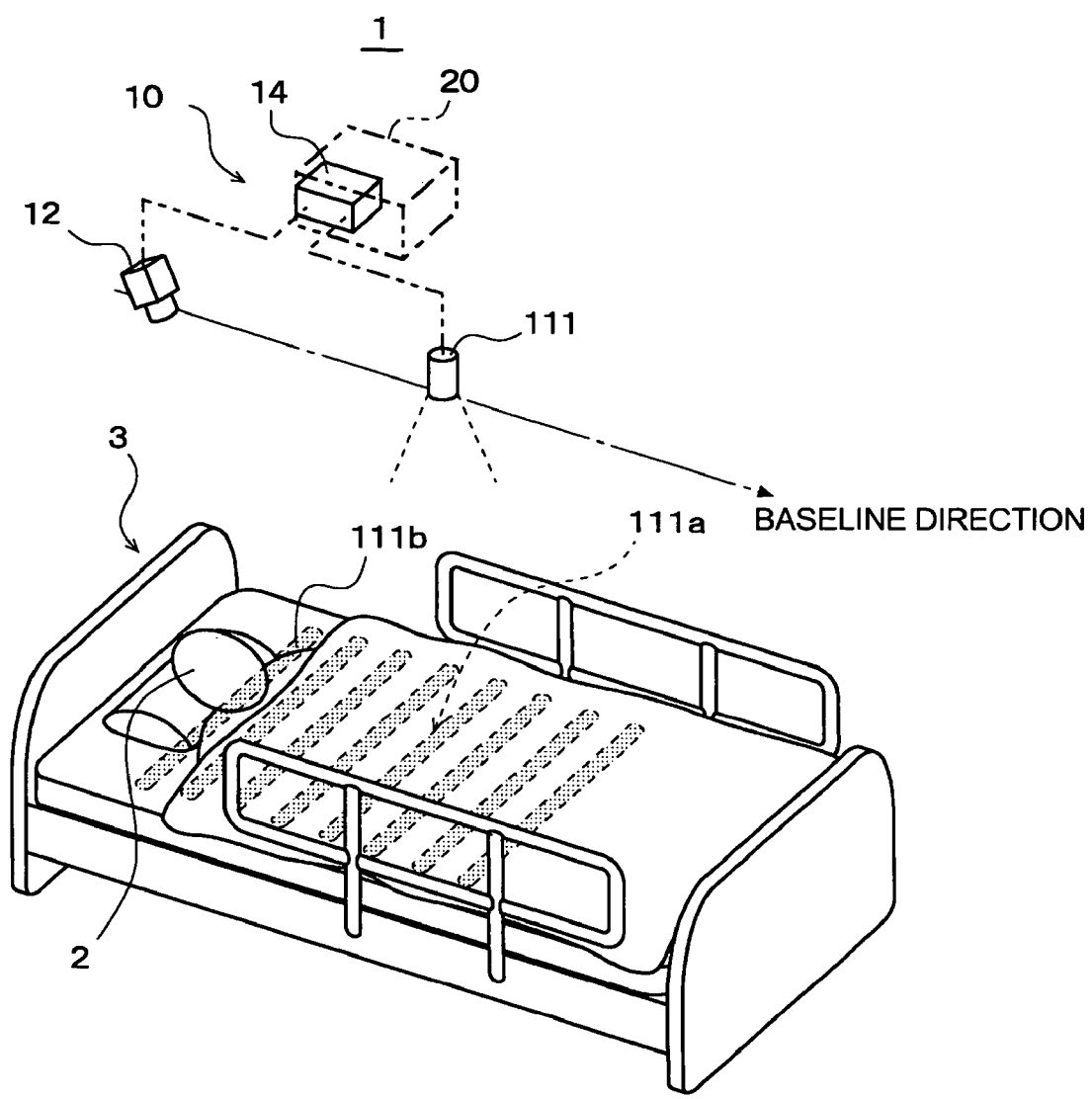
FIG. 14 is a schematic view of the external appearance of a monitoring apparatus, using a plurality of bright lines as a light pattern projected by a projecting device, according to an embodiment of the present invention.

While the above description is made assuming that the pattern projected on the bed 3 is made up of a plural number of bright spots, the pattern may be made up of bright lines as shown in FIG. 14. That is, the movement in the height direction of the person 2 may be measured using the optical tomography. In this case, a projecting device 111 is used that is constituted to project a light pattern of bright lines on the bed 3. While the number of bright lines to be projected is typically plural, it may be singular. The following is the explanation of using a plural number of bright lines. A plural number of bright lines 111*b* are projected at equal intervals. The bright lines 111*b* form a pattern 111*a*. The direction of the bright lines 111*b* is approximately vertical to the base line of triangulation.

Figure 15:
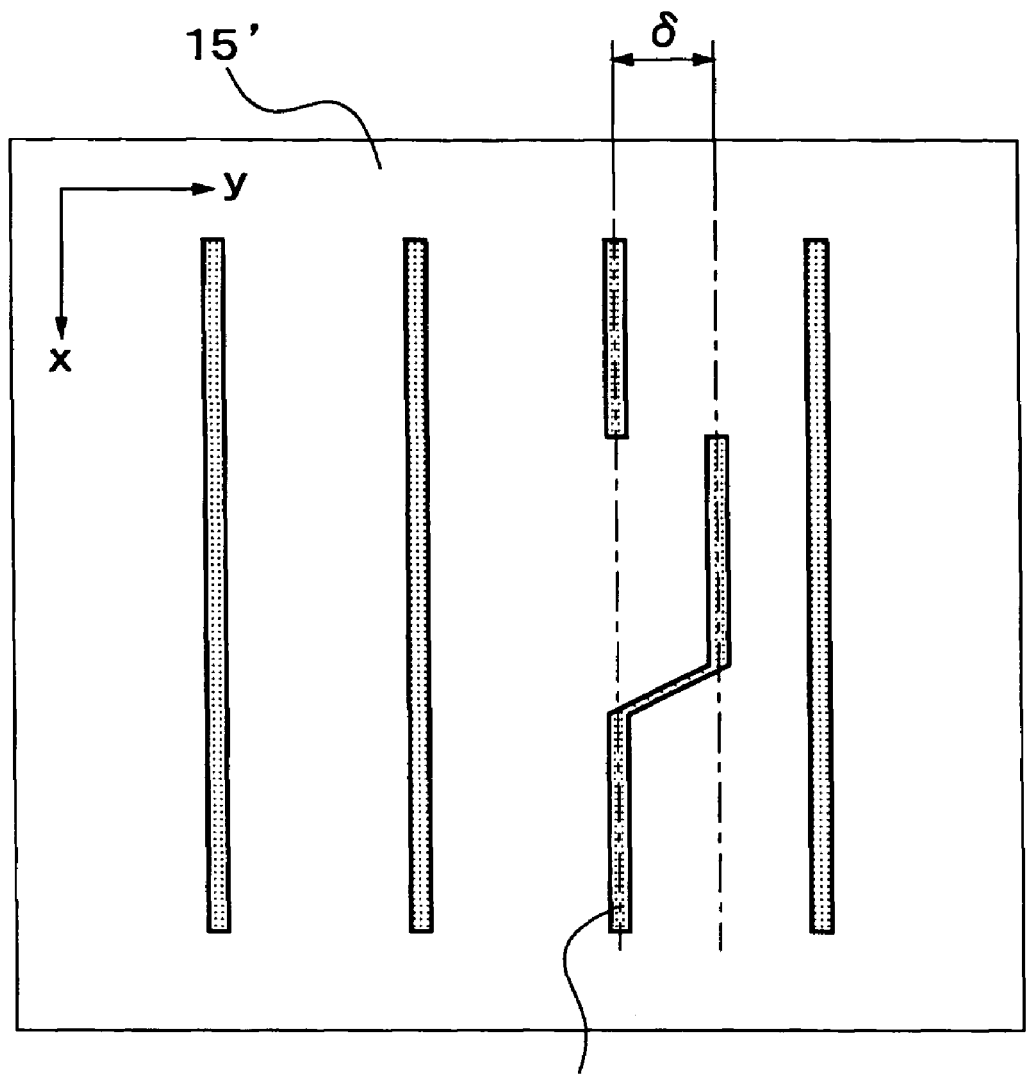
FIG. 15 is a schematic view illustrating the bright lines imaged on an image plane of FIG. 14.

When the bright lines are used as shown in FIG. 15, like when using the bright spots explained with FIG. 6, the presence of a solid of a height has it that the image of a bright line imaged on the image plane 15' of the image sensor device 15 moves by an amount of δ in the direction of y-axis. Further likewise, positions on the solid can be specified in three dimensions by the measurement of the δ. The measurement of the δ is carried out on the centerline of the image of the bright line. When the bright lines are used, the measurement point corresponds to one pixel of the image sensor device 15 located on the image of the bright line.

As described above, using the light pattern of a plural number of bright lines and measuring the shift of the bright lines make it possible, unlike using the light pattern of a plural number of bright spots, to measure the shift of any point on the bright line, so that continuous shape along the bright line direction can be recognized. In other words, measurement resolution in the direction of bright line is improved.

As described above, in the monitoring apparatus 1, the FG sensor 10 measures sampling-point-moves in the height direction of the person 2 existing on the bed 3 at a plurality of sampling points, and the area definition section 22 defines an area where a plurality of the sampling-point-moves measured are in the generally same phase. In addition, in this embodiment, the display 40 displays the defined area over a 3-D shape allowing recognition of the shape of the person 2. Thus, the state of the person 2, in particular the breathing state thereof, can be easily and accurately grasped. Further, the 3-D shape generation section 23 generates a 3-D shape allowing recognition of the body shape of the person 2, allowing the breathing state of the person 2 to be clearly grasped. The use of the FG sensor 10 as a 3-D sensor allows accurate measurement of sampling-point-moves in the height direction of the person 2 with a simple construction. Since the FG sensor 10 performs the measurement in a non-contact manner, the burden imposed on the person to be measured can be reduced.

If a specific number or more of the sampling points in a specific area represent sampling-point-moves in the same, specific type of phase, the area definition section 22 defines the specific area as an area where the sampling-point-moves in the specific type of phase are occurring. Thus, the monitoring apparatus 1 can distinguish the phases of sampling-point-moves in respective parts of the person 2. Also, parts of the person 2 with sampling-point-moves in the upward and downward phases can be distinguished. This is advantageous in the determination of a breathing anomaly of the person 2. This is also true in a case where the area definition section 22 searches a specific area for sampling points representing sampling-point-moves in the same, specific type of phase, forms a group of sampling points representing the sampling-point-moves in the generally same phase based on the search results, and defines the thus formed group of sampling points as an area where the sampling-point-moves in the generally same phase are occurring. Displaying sampling-point-moves in respective parts of the body of the person 2 over a 3-D shape showing the external shape of the body facilitates recognition of the sampling-point-moves in the respective parts of the body (in particular, sampling-point-moves associated with breaths). Such display can be referenced by a doctor for diagnosis, for example.

In a case where both an area with upward sampling-point-moves and that with downward sampling-point-moves are defined on the person 2 by the area definition section 22, the anomaly determination section 26 determines an anomaly of the person 2 based on the sampling-point-moves of the person 2 in the respective areas. In this manner, the monitoring apparatus 1 can determine sleep apnea syndrome. The anomaly determination section 26 determines the sleep apnea syndrome as central apnea if no overall movement is detected (immobility is determined), and as obstructive apnea if breaths in opposite phases are detected in the thorax and the abdomen. That is, the monitoring apparatus 1 can discriminate between the central apnea and the obstructive apnea.

The display 40 of the monitoring apparatus 1 displays the areas defined by the area definition section 22 over a 3-D shape allowing recognition of the shape of the person 2 in the above description. However, the display 40 may output, or display, information for each area defined by the area definition section 22. This can significantly reduce the amount to be processed and simplify the construction without the need for superimposed display. Also, in this case, since the 3-D shape generation section 23 is not necessary, the construction can be further simplified.

The invention claimed is:

1. A condition analysis apparatus comprising:
a three-dimensional sensor for measuring, at a plurality of sampling points, sampling-point-moves in a height direction of an object existing in a target area; and
area definition means for defining an area where a plurality of the sampling-point-moves are in generally a same phase, wherein the area definition means searches a specific area for sampling points representing the sampling-point-moves in the same specific type of phase, forms a group of the sampling points representing the sampling-point-moves in generally the same phase based on search results of the searching, and defines the formed group of sampling points as an area where the sampling-point-moves in generally the same phase are occurring; said three-dimensional sensor comprising:
a projection device for projecting a light pattern on the target area;
an image capturing apparatus for capturing an image of the target area while the light pattern is projected thereon, said image capturing apparatus being installed distanced from said projection device; and
measurement means for measuring shifts of the pattern on the captured images,
wherein sampling-point-moves in the height direction of the object are measured at the plurality of points based on the shifts of the pattern measured.

2. The condition analysis apparatus as recited in claim 1, further comprising:
information output means for outputting information of an area including the area defined by the area definition means.

3. The condition analysis apparatus as recited in claim 1, wherein, if a specific number or more of the sampling points in a specific area represent sampling-point-moves in the same specific type of phase, the area definition means defines the specific area as an area where the sampling-point-moves in the specific type of phase are occurring.

4. The condition analysis apparatus as recited in claim 2, wherein, if a specific number or more of the sampling points in a specific area represent sampling-point-moves in the same specific type of phase, the area definition means defines the specific area as an area where the sampling-point-moves in the specific type of phase are occurring.

5. The condition analysis apparatus as recited in claim 1, wherein the area definition means is further for defining two or more areas in different phases, defining a boundary between the two or more areas, and defining the areas divided by the boundary as new areas.

6. The condition analysis apparatus as recited in claim 2, wherein the area definition means is further for defining two or more areas in different phases, defining a boundary between the two or more areas, and defining the areas divided by the boundary as new areas.

7. The condition analysis apparatus as recited in claim 1, further comprising:
anomaly determination means for determining an anomaly of the object based on the area defined by the area definition means.

8. The condition analysis apparatus as recited in claim 2, further comprising:
anomaly determination means for determining an anomaly of the object based on the area defined by the area definition means.

* * * * *